(12) United States Patent
Schwartz et al.

(10) Patent No.: US 9,480,636 B2
(45) Date of Patent: Nov. 1, 2016

(54) SKIN LIGHTENING FORMULATIONS

(71) Applicant: ROHM AND HAAS COMPANY, Philadelphia, PA (US)

(72) Inventors: Curtis Schwartz, Ambler, PA (US); Nilesh Shah, Maple Glen, PA (US); Theodore Tysak, Ambler, PA (US)

(73) Assignee: Rohm and Haas Company, Philadelphia, PA (US)

( * ) Notice: Subject to any disclaimer, the term of this patent is extended or adjusted under 35 U.S.C. 154(b) by 8 days.

(21) Appl. No.: 14/368,552

(22) PCT Filed: Dec. 19, 2012

(86) PCT No.: PCT/US2012/070447
§ 371 (c)(1),
(2) Date: Jun. 25, 2014

(87) PCT Pub. No.: WO2013/101570
PCT Pub. Date: Jul. 4, 2013

(65) Prior Publication Data
US 2015/0098919 A1    Apr. 9, 2015

Related U.S. Application Data

(60) Provisional application No. 61/580,430, filed on Dec. 27, 2011.

(51) Int. Cl.
*A61K 8/18* (2006.01)
*A61K 8/81* (2006.01)
*A61Q 19/02* (2006.01)
*A61K 8/86* (2006.01)

(52) U.S. Cl.
CPC ............... *A61K 8/8152* (2013.01); *A61K 8/86* (2013.01); *A61Q 19/02* (2013.01); *A61K 2800/594* (2013.01)

(58) Field of Classification Search
None
See application file for complete search history.

(56) References Cited

U.S. PATENT DOCUMENTS

| | | | |
|---|---|---|---|
| 2004/0062913 A1 | 4/2004 | Suto et al. | |
| 2005/0100570 A1 | 5/2005 | Wei et al. | |
| 2006/0018861 A1 | 1/2006 | Chen et al. | |
| 2010/0008883 A1* | 1/2010 | Alwattari | A61K 8/416 424/70.13 |

FOREIGN PATENT DOCUMENTS

| | | |
|---|---|---|
| WO | 2005/065638 A1 | 7/2005 |
| WO | 2006/020163 A1 | 2/2006 |
| WO | 2011/008631 A2 | 1/2011 |
| WO | 2011/064383 A1 | 6/2011 |

* cited by examiner

*Primary Examiner* — Nannette Holloman
(74) *Attorney, Agent, or Firm* — Edward L. Brant

(57) ABSTRACT

A skin care formulation which provides a skin lightening effect virtually immediately upon topical application to the skin and which includes a combination of one or more poly(ethylene) oxides and an acrylic emulsion polymer film former comprising emulsion polymers derived from one or more ethylenically unsaturated monomers.

6 Claims, No Drawings

SKIN LIGHTENING FORMULATIONS

CROSS-REFERENCE TO RELATED APPLICATIONS

This application claims priority to and is a 371 U.S.C. §371 national phase application of International Application No. PCT/US12/070,447, filed on Dec. 19, 2012, which claims priority from U.S. Provisional Application Ser. No. 61/580,430, filed Dec. 27, 2011, both of which are incorporated herein by reference in their entireties.

FIELD OF THE INVENTION

The present invention relates to skin care formulations which produce skin lightening or whitening effects upon application. The skin care formulations are aqueous and contain one or more water soluble poly(ethylene oxide) resins and one or more polymer film formers.

BACKGROUND OF THE INVENTION

Many formulations are available for application to the skin for various effects including cosmetic effects and medicinal treatment, or even both purposes concurrently. Such formulations exist in the form of liquids, gels, lotions, creams, ointments, mists, sprays, etc.

One reason for treating skin is to alter its color or tone, such as by lightening (whitening), or darkening (or tanning). Various conditions of the skin, including genetic, injury and disease, irritation, sometimes cause areas of undesirable discoloration such as age spots, burns, blotches, rashes, scar tissue, birth marks, and other things often give rise to the desire to alter skin color. Additionally, purely aesthetic concerns sometimes underlay the desire to alter skin color to achieve more even tone, lighter tone or darker tone.

Just as there are tanning lotions and sprays which darken skin tone, there are also skin lightening formulations which are used to lighten or whiten skin tone. While some such skin care formulations take time to produce the desired skin lightening effect, consumers would appreciate also having skin care formulations available which produce lightening or whitening effects quickly, and even immediately.

For example, US Patent Application Publication No. 2006/0018861 discloses a skin care composition for lightening skin tone which comprises a flavanoid component, a vitamin B3 compound, and an oil-in-water carrier, as well as various other optional ingredients. The combination of the flavanoid and vitamin B3 is described as providing a synergistic skin lightening effect. US Patent Application Publication No. 2006/0018861 also describes the use of more conventional skin tone changing and lightening agents, such as pigments, reflective particulate material and mixtures thereof. More specifically, examples of suitable pigments include talc, mica, silica, magnesium silicate, titanium oxide and zinc oxide. Examples of suitable reflective particulate materials include inorganic compounds such as titanium dioxide and zinc oxide. Other typical skin lightening agents mentioned in US Patent Application Publication No. 2006/0018861 include active ingredients that improve hyperpigmentation, including ascorbic acid compounds, azelaic acid, butyl hydroxyanisole, gallic acid and its derivatives, glycyrrhizinic acid, hydroquinone, kojic acid, arbutin, mulberry extract, and mixtures thereof. It is also pointed out that use of combinations of skin lightening agents is believed to be advantageous in that they may provide skin lightening benefit through different mechanisms. US Patent Application Publication No. 2006/0018861 further suggests that poly(ethylene) oxides and carboxylic acid/carboxylate copolymers are both among various compounds useful as viscosifying agents in the skin care composition described therein, though there is no indication that such compounds contribute in any way to the desired skin lightening effect.

The skin care industry would welcome alternative formulations that produce skin lightening or whitening effects that do not require particulate ingredients, such as pigments and reflective materials, or acidic ingredients such as those mentioned above. The present invention provides a skin care formulation which provides a skin lightening effect virtually immediately upon topical application to the skin and which includes a combination of one or more poly(ethylene) oxides and an acrylic emulsion polymer film former comprising emulsion polymers derived from one or more ethylenically unsaturated monomers.

SUMMARY OF THE INVENTION

The present invention provides a skin care formulation which lightens skin tone upon topical application to skin. The skin care formulation comprises: A) 0.5 to 10% by weight of an emulsion polymer film former; B) 0.05 to 1% by weight of a poly(ethylene oxide) resin having the general formula $[-CH_2CH_2O-]_n$, wherein n=1,000-200,000; C) 2 to 70%, by weight, of one or more moisturizing agents; and D) 0.1 to 15%, by weight, of one or more stabilizers. The poly(ethylene oxide) resin comprises polymerized units derived from ethylene oxide. The emulsion polymer film former is a polymer comprising polymerized units derived from one or more ethylenically unsaturated monomers.

The present invention also provides a method for lightening skin tone, comprising applying one or more coats to skin of the above-described skin care formulation, and allowing each coat to dry prior to application of subsequent coat.

DETAILED DESCRIPTION OF THE INVENTION

"Polymer," as used herein, means a polymeric compound prepared by polymerizing monomers, whether of the same or a different type. The generic term "polymer" includes the terms "homopolymer," "copolymer," and "terpolymer." Also, as used herein, the terms "resin" and "polymer" are synonymous.

The term "polymerized units derived from" as used herein refers to polymer molecules that are synthesized according to polymerization techniques wherein a product polymer contains "polymerized units derived from" the constituent monomers which are the starting materials for the polymerization reactions. Furthermore, herein, endpoints of ranges are considered to be definite and are recognized to incorporate within their tolerance other values within the knowledge of persons of ordinary skill in the art, including, but not limited to, those which are insignificantly different from the respective endpoint as related to this invention (in other words, endpoints are to be construed to incorporate values "about" or "close" or "near" to each respective endpoint). The range and ratio limits, recited herein, are combinable. For example, if ranges of 1-20 and 5-15 are recited for a particular parameter, it is understood that ranges of 1-5, 1-15, 5-20, or 15-20 are also contemplated and encompassed thereby.

All percentages stated herein are weight percentages, unless otherwise stated.

The present invention provides skin care formulations which lighten (or whiten) skin tone (or color) upon topical application to skin, and which comprise:
- A) 0.5 to 10% by weight of an emulsion polymer film former;
- B) 0.05 to 1% by weight of a poly(ethylene oxide) resin having the general formula [—CH$_2$CH$_2$O—]$_1$, wherein n=1,000-200,000;
- C) 2 to 70%, by weight, of one or more moisturizing agents; and
- D) 0.1 to 15%, by weight, of one or more stabilizers.

Without wishing to be bound by theory, it is believed that it is the interaction of the emulsion polymer film former with the poly(ethylene oxide) resin in a topically applied, leave-on skin care formulation results in a destabilization of the emulsion polymer film former during the drying process on the skin, which results in an instant or triggered coagulation. The resulting dispersed coagulation scatters light, and gives the skin lightening effect. More particularly, although PEO resins are already known and used as viscosifying agents and for sensory enhancement in various personal care formulations, it is surprising that only a low amount, i.e., 0.05 to 1% by weight, of the PEO resin, along with less than about 10% by weight of the emulsion polymer film former, are able to produce the instant skin whitening effect. Emulsion polymer film formers suitable for use in the skin care formulation of the present invention are emulsion polymers derived from one or more ethylenically unsaturated monomers. The emulsion polymer film former may also comprise one or more of the following components: acid functional residues, polyvalent metal ion and complex crosslinking agents.

Suitable emulsion polymer film formers have glass transition temperatures, $T_g$, from -1 to 120° C., such as from 25° C. to 90° C., or from 40° C. to 80° C., or even from 50° C. to 75° C. The "glass transition temperature," or "$T_g$," as used herein, means the temperature at or above which a glassy polymer will undergo segmental motion of the polymer chain. Glass transition temperatures of a polymer can be estimated by the Fox Equation (Bulletin of American Physics Society, 1 (3), p 123, 1956), as follows:

$$1/T_g = w_1/T_{g,1} + w_2/T_{g,2}$$

For a copolymer comprising two type of monomers, $w_1$ and $w_2$ refer to the weight fraction of the two monomers, and $T_{g,1}$ and $T_{g,2}$ refer to the glass transition temperatures of the two corresponding homopolymers made from the monomers. For polymers containing three or more monomers, additional terms are added ($w_n/T_{g,n}$). The $T_g$ of a polymer can also be measured by various techniques including, for example, differential scanning calorimetry (DSC).

In some embodiments, skin care formulations in accordance with the present invention comprise from 0.5 to 10%, such as from 0.5 to 5%, or even from 0.25 to 2.5%, by weight, of the emulsion polymer film former, based on the total weight of the skin care formulation.

The emulsion polymer film former may be one or more acrylic polymers or copolymers such as polyacrylates, polymethacrylates and copolymers thereof, vinyl polymers such as polyvinylpyrrolidones, copolymers of methyl vinyl ether and of maleic anhydride, the copolymer of vinyl acetate and of crotonic acid, copolymers of vinylpyrrolidone and of vinyl acetate, copolymers of vinylpyrrolidone and of caprolactam, and polyvinyl alcohols.

Methods for preparation of the emulsion polymer film formers suitable for use in the skin care formulation of the present invention are known in the art and not especially limited. The preparation method may be selected from solution, dispersion and emulsion polymerization processes. Emulsion polymerization is especially useful for preparing useful polymer film formers. The practice of emulsion polymerization is well known and discussed in detail in the literature, for example, in D. C. Blackley, *Emulsion Polymerization* (Wiley, 1975). The polymerization temperature is typically from ambient temperature up to 90° C. and may also involve use of dispersing agents, initiators, accelerators, emulsifiers, chain transfer agents. As will be readily understood by persons of ordinary skill, dispersing agents may include anionic or nonionic dispersing agents, polymerization initiators may be of the free radical type, such as ammonium or potassium persulphate. The initiators may be used alone or with an accelerator, such as potassium metabisulphite or sodium thiosulphate. Examples of suitable emulsifiers during polymerization include, for example, alkaline metal and ammonium salts of alkyl, aryl, alkaryl and aralkyl sulphonates, sulphates, polyether sulphates, and alkoxylated derivatives of fatty acids, esters, alcohols, amines, amides and alkylphenols. Chain transfer agents, including mercaptans, polymercaptans and polyhalogen compounds may be used in the polymerization mixture to control molecular weight of the polymer.

Suitable emulsion polymer film formers may contain, as polymerized units, from 5% to 90%, such as from 5% to 80%, from 5% to 50%, or even from 10 to 20%, by weight based on the total weight of the emulsion polymer film former, of one or more monoethylenically unsaturated monomers containing an acidic functional group selected from one or more of carboxylic, sulfonic and phosphonic groups. For example, suitable carboxylic acid monomers include, without limitation, monoethylenically unsaturated ($C_3$-$C_9$) carboxylic acid monomers, such as unsaturated monocarboxylic and dicarboxylic acid monomers. For example, unsaturated monocarboxylic acids include acrylic acid (AA), methacrylic acid (MAA), alpha-ethacrylic acid, beta-dimethylacrylic acid, vinylacetic acid, allylacetic acid, ethylidineacetic acid, propylidineacetic acid, crotonic acid, acryloxypropionic acid and alkali and metal salts thereof. Suitable unsaturated dicarboxylic acid monomers include, for example, maleic acid, maleic anhydride, fumaric acid, itaconic acid, citraconic acid, mesaconic acid, methylenemalonic acid and alkali and metal salts thereof.

Additional suitable monoethylenically unsaturated monomers containing sulfonic acid or phosphonic groups include, for example, 2-acrylamido-2-methyl-1-propanesulfonic acid, 2-methacrylamido-2-methyl-1-propanesulfonic acid, 3-methacrylamido-2-hydroxypropanesulfonic acid, allylsulfonic acid, methallylsulfonic acid, allyloxybenzenesulfonic acid, methallyloxybenzenesulfonic acid, 2-hydroxy-3-(2-propenyloxy)propanesulfonic acid, 2-methyl-2-propene-1-sulfonic acid, styrene-sulfonic acid, vinylsulfonic acid, 2-sulphoethyl methacrylate, 3-sulfopropyl acrylate, 3-sulfopropyl methacrylate, sulfomethyl acrylamide, sulfomethyl methacrylamide and phosphoethyl methacrylate.

As a further example, the one or more monoethylenically unsaturated monomers may comprise one or more (meth)acrylic monomers containing one or more pendant reactive functional groups selected from hydroxy, thiol, and amino groups. Suitable hydroxy-functional (meth)acrylic monomers include, for example, hydroxyl ($C_1$-$C_4$)alkyl (meth)acrylates, such as hydroxyethyl methacrylate, hydroxyethyl acrylate, hydroxypropyl methacrylate and hydroxypropyl acrylate. Suitable amino-functional (meth)acrylic monomers include, for example, dimethylaminopropyl methacrylamide, dimethylaminopropyl acrylamide, dimethylaminoethyl methacrylate, dimethylaminoethyl acrylate, dimethylaminopropyl methacrylate and dimethylaminopropyl acrylate. Suitable thiol-functional (meth)acrylic monomers include, for example, 2-mercaptopropyl methacrylate.

As a still further example, the one or more monoethylenically unsaturated monomers may comprise one or more $(C_1-C_{20})$alkyl (meth)acrylate ester monomers, such as, without limitation, methyl acrylate, ethyl acrylate, propyl acrylate, isopropyl acrylate, butyl acrylate, isobutyl acrylate, secondary butyl acrylate, tertiary-butyl acrylate, methyl methacrylate, ethyl methacrylate, propyl methacrylate, isopropyl methacrylate, cyclopropyl, methacrylate, butyl methacrylate and isobutyl methacrylate, hexyl and cyclohexyl methacrylate, cyclohexyl acrylate, isobornyl methacrylate, 2-ethylhexyl acrylate (EHA), 2-ethylhexyl methacrylate, octyl (meth)acrylate, decyl (meth)acrylate, isodecyl (meth)acrylate, undecyl (meth)acrylate, dodecyl (meth)acrylate (also known as lauryl (meth)acrylate), tridecyl (meth)acrylate, tetradecyl (meth)acrylate (also known as myristyl (meth)acrylate), pentadecyl (meth)acrylate, hexadecyl (meth)acrylate (also known as cetyl (meth)acrylate), heptadecyl (meth)acrylate, octadecyl (meth)acrylate (also known as stearyl (meth)acrylate), nonadecyl (meth)acrylate, eicosyl (meth)acrylate and combinations thereof. Typically, the $(C_1-C_{20})$alkyl (meth)acrylate esters are $(C_1-C_8)$alkyl (meth)acrylate esters and preferably $(C_1-C_8)$alkyl acrylate esters; more preferably, the $(C_1-C_{20})$alkyl (meth)acrylate esters are selected from methyl acrylate, ethyl acrylate, butyl acrylate and 2-ethylhexyl acrylate; most preferably, the acrylate esters are selected from butyl acrylate and 2-ethylhexyl acrylate.

The one or more monoethylenically unsaturated monomers used to prepare the emulsion polymer film formers, may comprise one or more vinylaromatic monomers, such as, for example, styrene, alpha-methyl styrene and substituted styrenes, such as vinyl toluene, 2-bromostyrene, 4-chlorostyrene, 2-methoxystyrene, 4-methoxystyrene, alpha-cyanostyrene, allyl phenyl ether and allyl tolyl ether.

It is also possible for the emulsion polymer film formers to comprise, as polymerized units, 0 to 50%, such as 0 to 25%, by weight, based on the total weight of the emulsion polymer film former, of one or more other copolymerizable monomers. Suitable other copolymerizable monomers include, for example, butadiene, acrylonitrile, methacrylonitrile, crotononitrile, alpha-chloroacrylonitrile, ethyl vinyl ether, isopropyl vinyl ether, isobutyl vinyl ether, butyl vinyl ether, diethylene glycol vinyl ether, decyl vinyl ether, ethylene, methyl vinyl thioether and propyl vinyl thioether, esters of vinyl alcohol, and amides of ethylenically unsaturated $(C_3-C_6)$carboxylic acids, amides of ethylenically unsaturated $(C_3-C_6)$carboxylic acids that are substituted at the nitrogen by one or two $(C_1-C_4)$alkyl groups, acrylamide, methacrylamide and N-methylol (meth)acrylamide.

Poly(ethylene oxide) ("PEO") resins suitable for use in the skin care formulations of the present invention and described in further detail hereinafter, are non-ionic and comprise polymerized units derived from ethylene oxide. They may also comprise units derived from other monomers such as propylene oxide, in addition to ethylene oxide. The PEO resins may have a solubility in water of from 0.1% to 100%, at 20° C. and atmospheric pressure.

More particularly, PEO resins suitable for use in the present invention have the general formula [—CH$_2$CH$_2$O—]$_n$, wherein n=1,000 to 200,000, for example, 1,000 to 100,000, or even 1,000 to 50,000. Furthermore, suitable the PEO resin component has a weight average molecular weight, MW$_w$, of 50,000 to 8,000,0000 grams per mole (g/mol), such as 75,000 to 4,000,000 g/mol, or even 100,000 to 1,000,000 g/mol.

In some embodiments, the skin care formulation may comprise from 0.05 to 1%, such as from 0.1 to 1%, or even from 0.1 to 0.25%, by weight, of the PEO resin, based on the total weight of the skin care formulation.

Methods for preparing poly(ethylene oxide) resins suitable for use in the aqueous coating compositions of the present invention are familiar to persons of ordinary skill in the relevant art and are not particularly limited. For example, heterogeneous coordination anionic polymerization of ethylene oxide in non-solvent diluents, in the presence of a catalyst, would be suitable for preparation of water soluble poly(ethylene oxide) resins. Catalysts known to facilitate such anionic polymerization including bases such as hydroxides, carbonates or other compounds of alkali or alkaline earth metals, or even those based on zinc. Additionally, cationic polymerization of ethylene oxide may be performed to obtain water soluble poly(ethylene oxide) resins, in the presence of catalysts including protonic acids (HClO$_4$, HCl), Lewis acids (SnCl$_4$, BF$_3$, etc.), organometallic compounds, or more complex reagents. It is also possible to prepare suitable poly(ethylene oxide) resins from ethylene oxide by a ring-opening polymerization process using organo-metallic catalysts. Of course, where resins comprising polymerized units derived from ethylene oxide and another monomer, such as propylene oxide, is desired, both types of monomers should be present in the reactant mixture undergoing polymerization.

Commercial PEO resins found to be successful for modifying the gloss/appearance of aqueous coating compositions include POLYOX™ resins, which are nonionic, water soluble, high molecular weight poly(ethylene oxide) polymers, available from The Dow Chemical Company of Midland, Mich., U.S.A. The different types and concentrations of suitable POLYOX compounds include, without limitation, POLYOX WSR N-10, POLYOX WSR N-80, POLYOX WSR N-750, POLYOX WSR N-3000, POLYOX WSR-205, POLYOX WSR-1105, POLYOX WSR N-12K, POLYOX WSR-301, POLYOX WSR Coagulant, POLYOX WSR-303, POLYOX WSR-308, UCARFLOC™ Polymer 300, UCARFLOC Polymer 302, UCARFLOC Polymer 304, UCARFLOC Polymer 309. For reference, representative POLYOX resins are listed in TABLE 1 below with their weight average molecular weights.

TABLE 1

| Type of POLYOX | Weight Average Molecular Weight* |
|---|---|
| Polyox WSR N-10 | 100,000 |
| Polyox WSR N-80 | 200,000 |
| Polyox WSR N-750 | 300,000 |
| Polyox WSR N-3000 | 400,000 |
| Polyox WSR N-12K | 1,000,000 |
| Polyox WSR N-60K | 2,000,000 |
| Polyox WSR-205 | 600,000 |
| Polyox WSR-301 | 4,000,000 |

*Based on rheological measurements.

Other commercially available PEO resin materials which may be suitable to enhance gloss control properties when formulated into coating compositions include, without limitation, ALKOX® resins from Meisei Chemical Works, LTD, of Kyoto, Japan. The ALKOX® resins have molecular weights ranging between 100,000 and 8,000,000. Particular examples of ALKOX® resins believed to be suitable are, for example, ALKOX R-150, ALKOX R-400, ALKOX R-1000, ALKOX E-30, ALKOX E-45, ALKOX E-60, ALKOX E-75, ALKOX E-100, ALKOX E-130, ALKOX E-160, ALKOX E-240, ALKOX E-300, ALKOX L-6, ALKOX L-8, ALKOX L-11 Additionally, the PEO® Water-Soluble Thermoplastic Resins such as PEO-27, PEO-18Z, PEO-15Z, PEO-8Z, PEO-4, PEO-3Z, PEO-2, PEO-1Z, available from Sumitomo Seika Chemicals Co., Ltd., of Osaka, Japan, are believed to be suitable PEO resins for use in the coating compositions of the present invention.

It is further noted that PEO resin materials which are copolymers of ethylene oxide with propylene oxide may also be suitable for enhancing gloss control properties in the coating compositions of the present invention. Such copolymers of ethylene oxide and propylene oxide include, without limitation, ALKOX resins such as ALKOX EP-10 and ALKOX EP-20, which are commercially available from Meisei Chemical Works, LTD, of Kyoto, Japan.

The skin care formulation of the present invention also comprises from 2 to 70%, by weight, of one or more moisturizing agents such as 25 to 45%, or even 10 to 30%, based on the total weight of the skin care formulation. The term "moisturizing agents" as used herein is intended to include substances often referred to by persons of ordinary skill as moisturizers, emollients and humectants.

Examples of moisturizing agents include, without limitation, $C_{1-20}$ alkyl esters of fatty acids, $C_{10-22}$ fatty acids, i.e., stearyl, palmityl, lauryl, myristyl), $C_{10-22}$ fatty alcohols (stearyl, palmityl, lauryl, myristyl, oleyl), and $C_{10-22}$ fatty alcohol ethers, $C_{16-22}$ alkanoic triglycerides (sunflower seed oil), sterols, i.e., cholesterol, soy sterol, silicones (dimethicone), petroleum jelly, mineral oils. Examples of humectants are polyhydric alcohols such as sorbitol, hexylene glycol, and glycerin.

For improved lubricity, other ingredients might be optionally added to the formulation, such as lanolin or its hydrolysis products, squalene, jojoba oil, $C_7$-$C_{40}$ straight and branched hydrocarbons such as isohexadecane, $C_1$-$C_{30}$ alcohol esters such as isopropyl isostearate, glycerides, alkylene glycol esters, propoxylated and ethoxylated derivatives, sugar ester such as sucrose polycottonseedate, vegetable oils such as coconut oil, hydrogenated vegetable oils, animal fats and oils, and $C_4$-$C_{20}$ alkyl ethers of polypropylene glycols, $C_1$-$C_{20}$ carboxylic acid esters of polypropylene glycols, and di-$C_8$-$C_{30}$ alkyl ethers.

For example, in some embodiments, one or more emollients selected from fatty alcohols may be used to provide skin conditioning benefits. Fatty alcohols can form structured networks with emulsifiers to provide increased viscosity, phase stability, and conditioning benefits. The fatty alcohols useful herein are a saturated, linear or branched fatty alcohol, selected from the group consisting of saturated, linear or branched $C_{12}$-$C_{30}$ fatty alcohols, a saturated, linear or branched $C_{12}$-$C_{30}$ diols, and mixtures thereof. Preferred fatty alcohols are cetyl alcohol, stearyl alcohol, and mixtures thereof.

The skin care formulation of the present invention further comprises one or more stabilizers, for dispersing and stabilizing the oily components, such as emollients, in the aqueous skin care formulation. The term "stabilizers" as used herein includes various types of stabilizers such as emulsifiers, thickeners and rheology modifiers A wide variety of stabilizers are suitable for use in the skin care formulation, including those now known and conventional, as well as those which may be developed in the future. As will be recognized and practicable by persons of ordinary skill in the relevant art, the selected emulsifier must be chemically and physically compatible with essential components of the composition, and provide the desired dispersion characteristics.

One or more stabilizers are included in the skin care formulation in an amount of from 0.1 to 15%, by weight, such as 1 to 10%, or even 0.5 to 10%, based on the total weight of the skin care formulation.

Examples of various stabilizers suitable for use in the skin care formulation of the present invention include, without limitation, various non-ionic and anionic surfactants such as sugar esters and polyesters, alkoxylated sugar esters and polyesters, $C_{10}$-$C_{30}$ fatty acid esters of $C_{10}$-$C_{30}$ fatty alcohols, alkoxylated derivatives of $C_1$-$C_{30}$ fatty acid esters of $C_1$-$C_{30}$ fatty alcohols, alkoxylated ethers of $C_1$-$C_{30}$ fatty alcohols, polyglyceryl esters of $C_1$-$C_{30}$ fatty acids, $C_1$-$C_{30}$ esters of polyols, $C_1$-$C_{30}$ ethers of polyols, alkyl phosphates, polyoxyalkylene fatty ether phosphates, fatty acid amides, acyl lactylates, soaps, and mixtures thereof. Suitable rheology modifiers or thickeners include, without limitation, those based on acrylic associative or non-associative rheology modifiers, polysaccharides, polyacrylamides, alkyl acrylate crosspolymers.

The skin care formulations of the present invention have a typical viscosity of from 10 to 10,000 centipoise.

In addition to the foregoing components, the skin care formula of the present invention may also comprise a solvent, preferably an aqueous solvent, such as water or a mixture comprising water and a light alcohol, or water and a glycol, in an amount up to 80% by weight based on the total weight of the formulation.

As with other, known skin care formulations, the formulations in accordance with the present invention may contain additional ingredients including, without limitation: antioxidants, UV absorbers, radical scavengers, chelating agents, vitamins and derivatives thereof, abrasives, astringents, fragrance, structuring agents, emulsifiers, solubilizing agents, buffering agents, thickeners, pH adjusters, pigments or colorants, and preservatives. Such additional ingredients are typically selected and used for providing further aesthetic or functional benefit to the skin care formulation or the skin to which it is applied, such as sensory benefits relating to appearance, smell, or feel, therapeutic benefits, or prophylactic benefits. The above-described required components may also, themselves, provide such benefits. Most, if not all, such additional components are well-known to persons of ordinary skill in the relevant art and their use is not particularly limited in connection with the present invention.

The following information is for general guidance only, since it is believed that persons of ordinary skill are already well-equipped and in the best position to assess which, if any, such additional components, known now or in the future, may be beneficial depending on the particular skin care formulation and its intended application.

Suitable UV absorbers include, for example, 2-ethylhexyl-p-methoxycinnamate (commercially available as PARSOL™ MCX), butylmethoxydibenzoyl-methane, 2-hydroxy-4-methoxybenzo-phenone, 2-phenylbenzimidazole-5-sulfonic acid, octyldimethyl-p-aminobenzoic acid, octocrylene, 2-ethylhexyl N,N-dimethyl-p-aminobenzoate, p-aminobenzoic acid, 2-phenylbenzimidazole-5-sulfonic acid, octocrylene, oxybenzone, homomethyl salicylate, octyl salicylate, 4,4'-methoxy-t-butyldibenzoylmethane, 4-isopropyl dibenzoylmethane, 3-benzylidene camphor, 3-(4-methylbenzylidene) camphor, EUSOLEX™ 6300, octocrylene, octyl methoxy cinnamate (OMC), avobenzone (commercially available as PARSOL™ 1789), and mixtures thereof. PARSOL™ products are available from DSM Nutritional Products, Inc., of Heerlen, The Netherlands. EUSOLEX™ products are available from Merck KGaA, of Darmstadt, Germany.

Suitable antioxidants include, for example, vitamin C or its derivatives, botanical actives, vitamin E, flavanoids, and mixtures thereof.

Suitable buffering agents (i.e., neutralizers) include sodium hydroxide, potassium hydroxide, aminomethylpropanol, among others.

Suitable preservatives include NEOLONE™ CapG (commercially available from the Dow Chemical Company of Midland, Mich., U.S.A.), as well as mixtures of methyl isothiazolinone with capryl alcohol or phenoxyy ethanol, as well as others familiar to persons of ordinary skill.

The use, application and benefits of the present invention will be clarified by the following discussion and description of exemplary embodiments and applications of the formulations of the present invention.

For example, without limitation, some embodiments of the skin care formulation of the present invention comprise ingredients and compounds of the type and in the amounts listed in the Proposed Composition Table below.

TABLE 2

Proposed Composition

| Ingredient Category | Weight % range | Specific Examples |
|---|---|---|
| Moisturizing ingredients | 2-70% | Stearyl, palmityl, lauryl, myristyl, oleyl, sunflower seed oil, cholesterol, soy sterol, dimethicone, petroleum jelly, mineral oils. |
| Emulsifier | 1-15% | Stearic acid, non-ionic and anionic surfactants, cationic surfactants, acrylic-based polymers |
| Emollient | 1-20% | Lanolin, squalene, jojoba oil and other oils and esters |
| Skin lightening active(s) | 0-10% | Kojic acid, vitamin C, hydroquinone |
| UV absorbing actives | 0-35% | Avobenzone, OMC, |
| Anti-oxidant actives | 0-5% | Vitamin C, botanicals, Vitamin E |
| Hollow Sphere Particles | 0-10% | SunSpheres ™ Polymer |
| Rheology modifier | 0-10% | Acrylic based polymers, xanthan gum |
| Neutralizer | 0-2% | NaOH, KOH, Aminomethylpropanol |
| Pigments or Colorants | 0-10% | Iron oxides |
| Silicone compound | 0-10% | Dimethicone |
| Stearic acid and salts | 0-10% | Thickener and skin feel agent |
| Polyolefin polymer | 0-5% | Conditioning agent, skin feel agent |
| Fatty alcohols | 0-5% | Thickener, skin feel agent |
| Water resistance agent | 0-2% | Hydrophobic polymers such as Soltex OPT ™ water resistance agent (trademark of Dow) |
| Solvent | 0-10% | Propylene glycol |
| Water, preservative, fragrance | Balance to 100% | |

EXAMPLES

Whitening (Lightening) Properties of Formulations

To test the whitening effect produced by formulations containing the combination of emulsion polymer film former and PEO resin, sample formulations were prepared according to the details provided in Table 3 and Table 4.

All the sample formulations had the components listed in the following TABLE 3 in common, in the listed amounts.

TABLE 3

Standard Test Formulation Components

| Material In Proper Order of Addition | Description/Function | Percent (By Weight) |
|---|---|---|
| Water | Diluent | 45.5* |
| Additive | Gloss Control | X* |
| KATHON ® CG/ICP | Preservative | 0.04 |
| CAPSTONE ™ FS-60 (1%) | Wetting Aid | 1.0 |
| Diethylene Glycol Ethyl Ether | Coalescing Solvent | 4.0 |
| Dipropylene Glycol Methyl Ether | Coalescing Solvent | 1.0 |
| Benzoflex ® 131 | Plasticizing Solvent | 1.0 |
| Tributoxy Ethyl Phosphate | Leveling Aid | 2.0 |
| Polymer (38%)** | Vehicle | 36.67 |
| Chemrez 30 (30%) | Alkali-Soluble Resin | 2.84 |
| Epolene ® E-43N (40%) | Polypropylene Wax Emulsion | 2.63 |
| A-C ®-325N (35%) | Polyethylene Wax Emulsion | 3.30 |
| SilFoam ® SE-21 | Defoamer | 0.02 |

*Water charge adjusted to provide 100% by weight of the formulation when additive added.
**Polymer Vehicle was a polymer prepared in accordance with the emulsion method described in U.S. Pat. No. 6,548,596, which is incorporated herein by reference. This polymer vehicle had a $T_g$ of 71.1° C. and comprised: 33% Butyl Methacrylate 10% Isobutyl Methacrylate 45% Styrene 12% Methacrylic Acid 1.5% zinc $T_{g(Fox)}$ 32 71.1° C.

Various sample formulations were prepared using the aforesaid standard test formulation components and various types and amounts of PEO as provided in TABLE 4 below.

TABLE 4

Whitening Agents Used In Whitening Effect Experiments

| Formulation # | PEO resin | Known Matting Agent | Amount (grams) |
|---|---|---|---|
| 1 | None | None | Standard |
| 2 | POLYOX WSR N-10 | | 0.25 |
| 3[Comp] | | ACEMATT TS-100[S] | 0.25 |
| 4 | POLYOX WSR N-205 | | 0.25 |

[Comp]Comparative Formulation not containing any PEO resin
[S]ACEMATT TS-100 is a silicon dioxide-based (CAS No. 112945-52-5) matting agent commercially available from Evonik Degussa Corporation of Parsippany, New Jersey 07054 U.S.A.

After completely mixing the ingredients (for 30 minutes), the PEO containing formulations were applied to leather pieces and black vinyl composite tiles, as described in further detail hereinafter.

Whiteness was measured using L* of the CIELAB (L*, a*, b*) color space, as determined using the following instrument:

BYK Spectro-Guide 45/0; Cat. No. 6801; Ser. No. 1059451

Manufactured by Byk-Gardner GMBH, 82538 Geretsried, Germany

L* is the coordinate on the scale of the three coordinates used in CIELAB that measures lightness (L*=0 yields black, and L*=100 indicates diffuse white). Thus, the higher the L* value, the whiter the color measured.

CIELAB is a color space specified by the International Commission on Illumination (French Commission internationale de l'éclairage). It describes all the colors visible to the human eye and was created to serve as an independent model to be used as a reference.

Whitening Effect (L*) on Leather Pieces

The sample formulations indicated in Table 4 were applied to leather pieces using a 3 mil (0.0762 millimeter)

Bird film applicator. The leather pieces were obtained from two different batches of natural leather. Each of the two leather samples had an area of 232 cm$^2$ and a thickness of 0.32 cm. Leather 1 was cowhide corrected grain leather and Leather 2 was cowhide full grain leather. Both leather samples were purchased from GST AutoLeather, located in Southfield, Mich., U.S.A.

Comparative Example 1

Leather 1 with no sample formulation coating applied.

Comparative Example 2

Leather 2 with no sample formulation coating applied

Example 1

One coating of sample Formulation 4 was applied to 2 pieces of Leather 1 and allowed to dry for seven days at 77° F. (25° C.) and 50% relative humidity. A second coat of sample formulation 4 was applied to one of these pieces of Leather 1 and allowed to dry as before.

Example 2

Repeat the procedure of Example 1 using sample Formulation 2 applied to 2 pieces of Leather 2.

The L* measurement results for leather pieces are presented in Table 5 below.

TABLE 5

| | Example Number | | | |
|---|---|---|---|---|
| | Comp. 1* | Comp. 2* | 1 | 2 |
| Formulation # | 1 | 1 | 4 | 3 |
| Substrate | Leather 1 | Leather 2 | Leather 1 | Leather 2 |
| Property Measured | | | | |
| 0 coat L* value | 64.27 | 48.88 | | |
| 1 coat L* value | | | 70.45 | 60.34 |
| 2 coat L* value | | | 75.31 | 66.21 |

*Comparative examples

Whitening Effect (L*) on Black Vinyl Tile

The sample formulations indicated in Table 5 were applied were applied to black vinyl composite tiles using a #38 wire wound rod. The black vinyl composite tiles measured 12 inches (305 mm)×12 inches (305 mm)×⅛ inch (3.2 mm) and were specifically Armstrong® Excelon® Vinyl Composition Tile Pattern 56790, manufactured by Armstrong World Industries, Inc, Lancaster, Pa. 17604]. One vinyl tile was left uncoated to provide a comparison Comparative Example 3

2 coats of sample Formulation 1, which contains no PEO resin or matting agent, were applied to vinyl tile. A drying time of one hour was permitted between the first and second coats and after the second coat prior to testing.

Comparative Example 4

2 coats of sample Formulation 3, which contains a known mattering agent instead of PEO resin, were applied to vinyl tile. A drying time of one hour was permitted between the first and second coats and after the second coat prior to testing.

Examples 3-4

The procedure of Comparative Example 4 was repeated, but using sample Formulations 4 and 2, respectively.

The L* measurement results for vinyl tiles are presented in Table 6 below.

TABLE 6

| | Example Number | | | |
|---|---|---|---|---|
| | Comp. 3* | Comp. 4* | 3 | 4 |
| Formulation # | 1 | 3$^{comp}$ | 4 | 2 |
| 2 coat L* value | 6.99 | 8.63 | 24.03 | 19.41 |

*Comparative examples

Exemplary Skin Care Formulation

The following Table 7 provides a list of ingredients and their amounts for producing a sample skin care formulation in accordance with the present invention for lightening skin tone upon topical application. This would be for a "leave-on" skin care product, as opposed to a wash-off product. Skin lightening effect would be observable immediately upon manual topical application of a homogenous layer of the skin care formulation to the skin.

TABLE 7

| Ingredient | Weight % | Functional Category |
|---|---|---|
| Polymer Vehicle* | 2.0 | Polymer emulsion |
| POLYOX WSR N-10 | 0.8 | PEO resin |
| Propylene Glycol | 3.0 | Moisturizer and Solvent |
| Glycerin | 2.0 | Humectant |
| Isopropyl Isostearate | 2.0 | Emollient |
| Caprylic/Capric Triglyceride | 3.0 | Emollient |
| *Macadamia Ternifolia* Seed Oil | 3.0 | Emollient |
| Pyrrolidone carboxylic acid Dimethicone | 2.0 | Moisturizer |
| Aculyn ™ 88 rheology modifier | 3.0 | Stabilizer |
| Di-polypropylene glycol-2-Myreth-10 Adipate | 1.5 | Emollient |
| Sodium hydroxide (10%) | 1.2 | Neutralizer |
| Tocopheryl Acetate | 0.2 | Anti-oxidant |
| NEOLENE ™ MxP | 0.5 | Preservative |
| Deioized Water | 75.8 | Water |

*Polymer Vehicle was a polymer prepared in accordance with the emulsion method described in U.S. Pat. No. 6,548,596, which is incorporated herein by reference. This polymer vehicle had a $T_g$ of 71.1° C. and comprised: 33% Butyl Methacrylate 10% Isobutyl Methacrylate 12% Methacrylic Acid 45% Styrene The above-listed ingredients are combined in the amounts shown and blended together until a homogeneous formulation is achieved, for example, for between 10 and 90 minutes. Often, a mixing time between 20 and 60 minutes is sufficient. Thereafter, the skin care formulation is applied directly to the skin surface, in even coats or layers.

What is claimed is:

1. A skin care formulation which lightens skin tone upon topical application to skin, consisting of:
    A) 0.5 to 10% by weight of an emulsion polymer film former;
    B) 0.05 to 0.25% by weight of a poly(ethylene oxide) resin having the general formula [—CH$_2$CH$_2$O—]$_n$, wherein n=1,000-200,000;
    C) 2 to 70% by weight of one or more moisturizing agents; and
    D) 0.1 to 15% by weight of one or more stabilizers.

2. The skin care formulation according to claim 1, wherein said poly(ethylene oxide) resin comprises polymerized units derived from ethylene oxide.

3. The skin care formulation according to claim 1, wherein said water soluble poly(ethylene oxide) resin has a weight average molecular weight of from 50,000 to 8,000,000.

4. The skin care formulation according to claim 1, wherein said emulsion polymer film former is a polymer comprising polymerized units derived from one or more monoethylenically unsaturated monomers.

5. A method for lightening skin tone, comprising applying one or more coats to skin of the skin care formulation of claim 1, and allowing each coat to dry prior to application of subsequent coat.

6. The skin care formulation according to claim 4, wherein said one or more monoethylenically unsaturated monomers are selected from the group consisting of acrylic acid, methacrylic acid, alpha-ethacrylic acid, beta-dimethylacrylic acid, vinylacetic acid, allylacetic acid, ethylidineacetic acid, propylidineacetic acid, crotonic acid, acryloxypropionic acid, maleic acid, maleic anhydride, fumaric acid, itaconic acid, citraconic acid, mesaconic acid, methylenemalonic acid, 2-acrylamido-2-methyl-1-propanesulfonic acid, 2-methacrylamido-2-methyl-1-propanesulfonic acid, 3-methacrylamido-2-hydroxypropanesulfonic acid, allylsulfonic acid, methallylsulfonic acid, allyloxybenzenesulfonic acid, methallyloxybenzenesulfonic acid, 2-hydroxyl-3-(2-propenylox)propanesulfonic acid, 2-methyl-2-propene-1-sulfonic acid, styrene-sulfonic acid, vinylsulfonic acid, 2-sulphoethyl methacrylate, 3-sulfopropyl acrylate, 3-sulfopropyl methacrylate, sulfomethyl acrylamide, sulfomethyl mehtacrylamide, phosphoethyl methacrylate, hydroxyethyl methacrylate, hydroxyethyl acrylate, hydroxypropyl methacrylate, hydroxypropyl acrylate, methyl acrylate, ethyl acrylate, propyl acrylate, isopropyl acrylate, butyl acrylate, isobutyl acrylate, secondary butyl acrylate, tertiary-butyl acrylate, methyl methacrylate, ethyl methacrylate, propyl methacrylate, isopropyl methacrylate, cyclopropyl, methacrylate, butyl methacrylate and isobutyl methacrylate, hexyl and cyclohexyl methacrylate, cyclohexyl acrylate, isobornyl methacrylate, 2-ethylhexyl acrylate (EHA), 2-ethylhexyl methacrylate, octyl (meth)acrylate, decyl (meth)acrylate, isodecyl (meth)acrylate, undecyl (meth)acrylate, dodecyl (meth)acrylate, tridecyl (meth)acrylate, tetradecyl (meth)acrylate, pentadecyl (meth)acrylate, hexadecyl (meth)acrylate, heptadecyl (meth)acrylate, octadecyl (meth)acrylate, nanodecyl (meth)acrylate, eicosy (meth)acrylate, styrene, vinyl toluene, 2-bromostyrene, 4-chlorostyrene, 2-methoxystyrene, 4-methoxystyrene, alpha-cyanostyrene, ally phenyl ether, allyl tolyl ether, and combinations thereof.

* * * * *